United States Patent
Langford

(10) Patent No.: US 9,782,315 B2
(45) Date of Patent: Oct. 10, 2017

(54) SHROUD GUARD FOR SURGICAL TABLES

(71) Applicant: Wylie McCoy Langford, McKinney, TX (US)

(72) Inventor: Wylie McCoy Langford, McKinney, TX (US)

(*) Notice: Subject to any disclaimer, the term of this patent is extended or adjusted under 35 U.S.C. 154(b) by 337 days.

(21) Appl. No.: 14/714,788

(22) Filed: May 18, 2015

(65) Prior Publication Data

US 2015/0335512 A1    Nov. 26, 2015

Related U.S. Application Data

(60) Provisional application No. 62/001,262, filed on May 21, 2014.

(51) Int. Cl.
*A61G 13/10* (2006.01)
*A61G 13/06* (2006.01)
*A61B 6/04* (2006.01)

(52) U.S. Cl.
CPC ............. *A61G 13/10* (2013.01); *A61G 13/06* (2013.01); *A61B 6/04* (2013.01)

(58) Field of Classification Search
CPC ....................................................... A61G 13/10
USPC .................................. 5/0.601, 611, 613–614
See application file for complete search history.

(56) References Cited

U.S. PATENT DOCUMENTS 6,240,582 B1 *  6/2001  Reinke ................. A61B 6/0457
                                                    378/209
9,233,042 B1 *  1/2016  Freude ................... A61G 13/10

* cited by examiner

*Primary Examiner* — Fredrick Conley
(74) *Attorney, Agent, or Firm* — Pearne & Gordon LLP

(57) ABSTRACT

A shroud guard is provided for protecting a height adjustment mechanism used to raise and lower the height of an operating room table. The shroud guard includes a support frame secured to a table base of the operating room table. The support frame includes a bracket with an attachment member and an upstanding shield support secured to the attachment member. The attachment member is secured to the table base via a fastener to inhibit movement along the table base. A shield is removably secured to the upstanding shield support and extends transversely over the table base of the operating room table and across the height adjustment mechanism to inhibit foreign objects from contacting the height adjustment mechanism.

20 Claims, 5 Drawing Sheets

SHROUD GUARD FOR SURGICAL TABLES

CROSS-REFERENCE TO RELATED APPLICATIONS

This application claims the benefit of U.S. Provisional Application No. 62/001,262, filed May 21, 2014, the entire disclosure of which is hereby incorporated herein by reference.

FIELD OF THE INVENTION

The present invention relates generally to a guard device for surgical tables, and more particularly, to a shroud guard for protecting a height adjustment mechanism used to raise and lower the height of an operating room table.

BACKGROUND OF THE INVENTION

A number of operating room tables are height adjustable relative to the floor surface. The height of the operating room table can be raised and lowered as desired by the caregivers (e.g., doctor, surgeon, anesthesiologist, nurses, etc.). A height adjustment mechanism is supported by the table base and is used to raise and lower the height of the patient table surface relative to the table base. A telescoping shroud is often provided to protect the movable elements of the height adjustment mechanism, and may also provide protection for various electronic or computer controls of the table. However, the table base typically has varying widths and depths spanning across the floor surface, and is often used by medical personnel as storage space for various items. It is common for the stored items to contact the telescoping shroud, especially during movement of the height adjustment mechanism, which damages the shroud and renders the height adjustment mechanism (and the entire surgical table) inoperable.

This instant invention results from an attempt to provide an innovative device that minimizes or eliminates damage to the height adjustment mechanism and shroud that is traditionally caused by contact with foreign objects.

BRIEF SUMMARY OF THE INVENTION

The following presents a simplified summary of the invention in order to provide a basic understanding of some example aspects of the invention. This summary is not an extensive overview of the invention. Moreover, this summary is not intended to identify critical elements of the invention nor delineate the scope of the invention. The sole purpose of the summary is to present some concepts of the invention in simplified form as a prelude to the more detailed description that is presented later.

In accordance with one aspect of the present invention, a shroud guard is provided for protecting a height adjustment mechanism used to raise and lower the height of an operating room table. The shroud guard comprises a support frame secured to a table base of said operating room table. The support frame comprises a bracket with an attachment member and an upstanding shield support secured to the attachment member. The attachment member is secured to said table base via a fastener to inhibit movement along a longitudinal axis of said table base. A shield is removably secured to the upstanding shield support and extending transversely over said table base of said operating room table and across substantially all of said height adjustment mechanism to thereby inhibit foreign objects from contacting said height adjustment mechanism.

In accordance with another aspect of the present invention, a shroud guard is provided for protecting a height adjustment mechanism used to raise and lower the height of an operating room table. The shroud guard comprises a support frame secured to a table base of said operating room table. The support frame comprises a first bracket with a first attachment member and a first upstanding shield support secured to the first attachment member, and a second bracket with a second attachment member and a second upstanding shield support secured to the second attachment member. Each of the first and second attachment members are independently secured to said table base via repositionable fasteners to inhibit movement along a longitudinal axis of said table base. Each of the first and second upstanding shield supports comprise a channel extending between a pair of arms. A shield is removably secured fasteners to both of the first and second upstanding shield supports by being received within the respective channel of each of the first and second upstanding shield supports. The shield extends transversely over said table base of said operating room table and across substantially all of said height adjustment mechanism to thereby inhibit foreign objects from contacting said height adjustment mechanism.

It is to be understood that both the foregoing general description and the following detailed description present example and explanatory embodiments of the invention, and are intended to provide an overview or framework for understanding the nature and character of the invention as it is claimed. The accompanying drawings are included to provide a further understanding of the invention and are incorporated into and constitute a part of this specification. The drawings illustrate various example embodiments of the invention, and together with the description, serve to explain the principles and operations of the invention.

BRIEF DESCRIPTION OF THE DRAWINGS

The foregoing and other aspects of the present invention will become apparent to those skilled in the art to which the present invention relates upon reading the following description with reference to the accompanying drawings, in which.

DESCRIPTION OF EXAMPLE EMBODIMENTS

Figure 1:
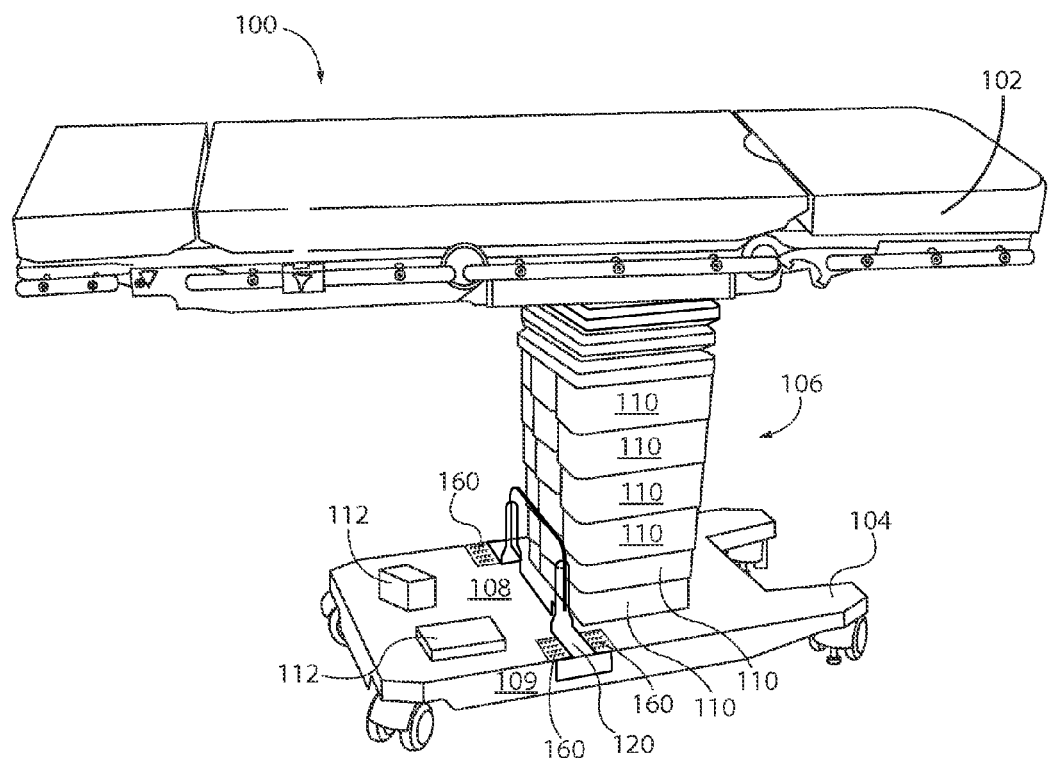
FIG. 1 illustrates a perspective view of one example shroud guard mounted upon a surgery table.

Example embodiments that incorporate one or more aspects of the present invention are described and illustrated in the drawings. These illustrated examples are not intended to be a limitation on the present invention. For example, one or more aspects of the present invention can be utilized in other embodiments and even other types of devices. Moreover, certain terminology is used herein for convenience only and is not to be taken as a limitation on the present invention. Still further, in the drawings, the same reference numerals are employed for designating the same elements.

The present application relates generally to a shroud guard for protecting the height adjustment mechanism, such as the telescoping shroud, used to raise and lower the height of an operating room table. Turning to FIG. 1, one example surgical table 100 is shown, although it is understood that the instant application could be used with any surgical table. The surgical table 100 includes a patient table surface 102 that is supported upon a table base 104 by a height adjustment mechanism 106. The table base 104 is supported upon a support surface, such as a ground surface. The height adjustment mechanism 106 is used to adjust the height of the patient table surface 102 relative to the table base 104 and the ground surface. A movable shroud 110 surrounds and protects the height adjustment mechanism 106. Often, the movable shroud 110 has a telescoping design, although various other configurations are contemplated. For example, the shroud 110 can be a telescoping column that has several layers (usually 4 to 7 layers), depending on manufacturer. The table base includes a base surface 108 that typically has varying widths and depths spanning across the floor, and is often used by medical personnel as storage space for various items 112 (e.g., SDC Machines, Arm Boards, Clark Sockets, Rail Clamps, etc.). A side surface 109 extends at least partially around the perimeter of the base surface 108. The side surface 109 may be arranged at an angle relative to the base surface 108, such as perpendicular or other angle. Additionally, the transition edge between the side surface 109 and base surface 108 may be sharp, angled, or curved.

Figure 2:
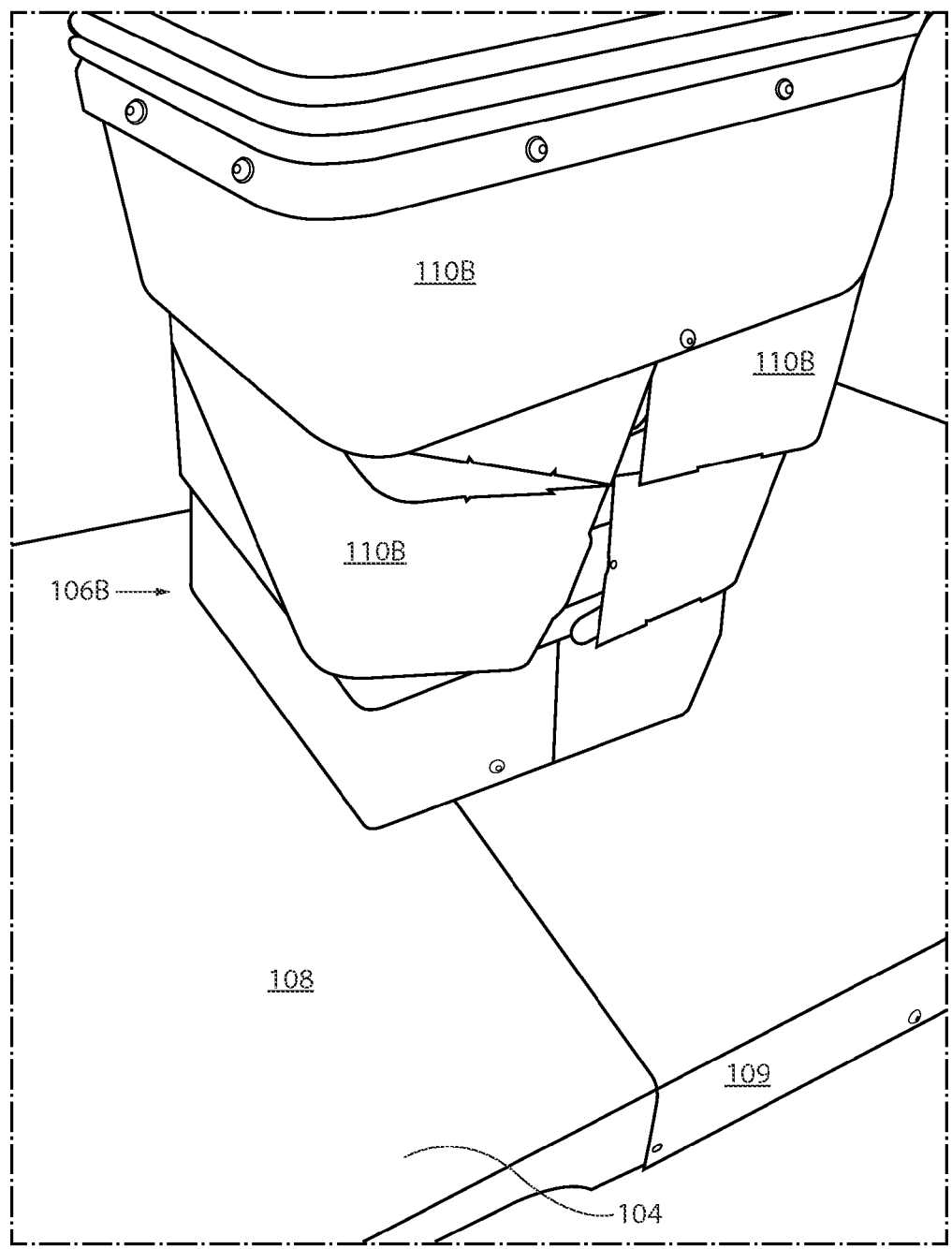
FIG. 2 illustrates a schematic example of a damaged height adjustment mechanism on a surgery table.

During surgery, items 112 are often placed on the table base 104 near the shroud 110, and often times things shift on the table base 104. As a result, it is common for the stored items 112 to contact the telescoping shroud 110, especially during movement of the height adjustment mechanism, which damages the shroud 110. For example, if the table is at a certain height and the surgeon requests for it to be lowered by the Anesthesia provider (who often controls table during surgery), the item(s) 112 nestled next to shroud 110 can catch and bend the lip of the shroud 110 (especially between telescoping layers). One example schematic depiction of a height adjustment mechanism 106B is provided in FIG. 2 showing damage to the various layers of the shroud 110B caused by contact with foreign objects. When this occurs, the entire surgical table is no longer of use because: (1) the height adjustment mechanism 106 is non-functional because the shroud 110 is bent and cannot move up or down; (2) the electronic controls and/or computer components of the table that are located inside the shroud 110 can be damaged; and/or (3) sterility is compromised.

Figure 3:
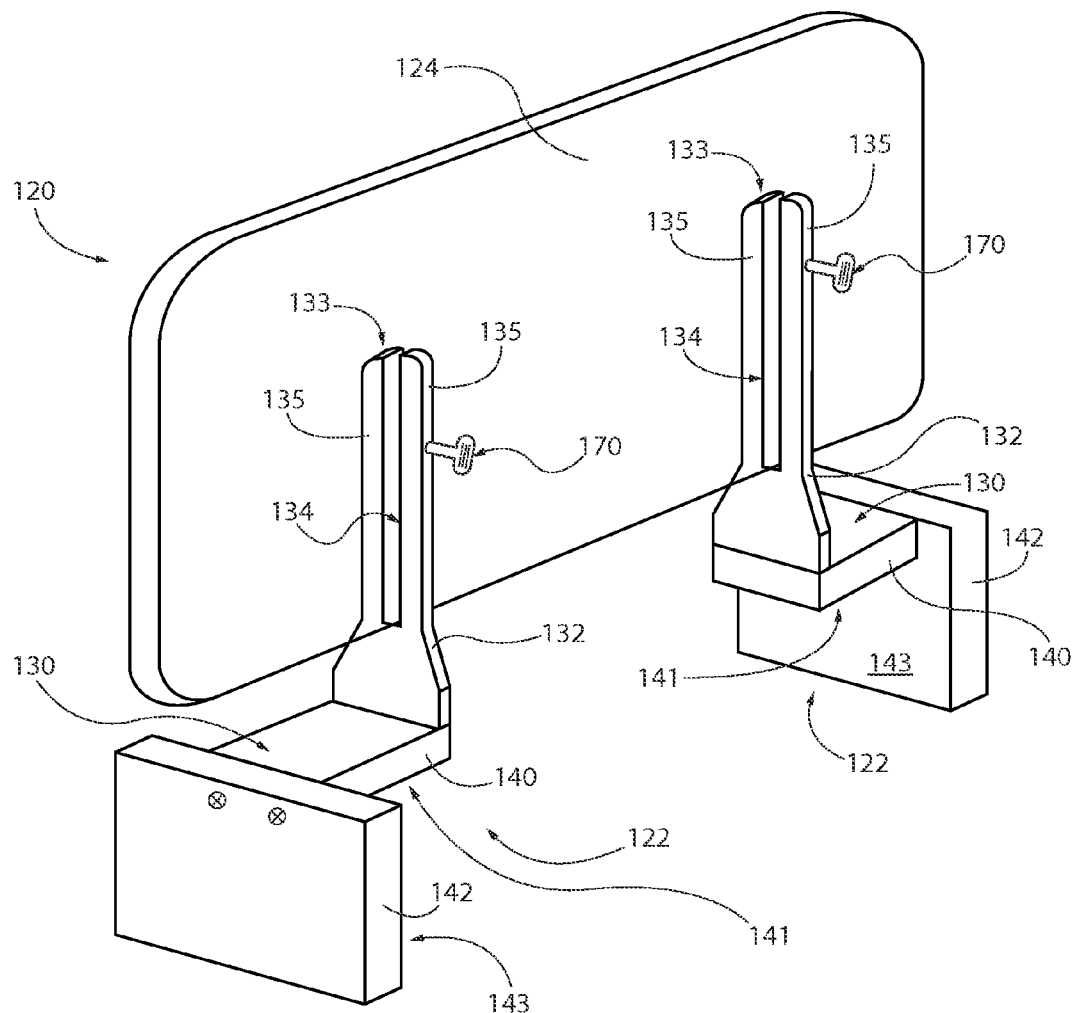
FIG. 3 illustrates a perspective view of an example shroud guard.

In order to avoid such damage to the height adjustment mechanism 106, the shroud guard 120 of the instant application includes at least two major elements. As shown in FIG. 3, the first element is a support frame 122, and the second element is a shield 124. The support frame 122 is used for the support and attachment of the shield 124 onto the base 104 of the surgical table 100.

The support frame 122 can include a pair of brackets each having an attachment member 130 that is secured onto the base 104 of the surgical table 100. Each attachment member 130 can have varying widths and depths spanning across the base surface 108 of the table base 104. The use of a pair of separate brackets that are independently adjustable can be beneficial to allow adjustment of the width therebetween by sliding either or both along the transverse width of the table base 104. In this manner, the brackets can be laterally slidable (i.e., perpendicular to a longitudinal axis of the table base) on the base surface 108 to be width-adjustable to be more useful with different tables having different widths and configurations. Each attachment member 130 is preferably made of durable, rigid materials that are suitable for use in an operating room and surgical setting, such as various metals (e.g., stainless steel, aluminum, etc.) and plastics. Such materials are easily cleaned and sterilized, and may or may not be radiolucent.

Figure 4:
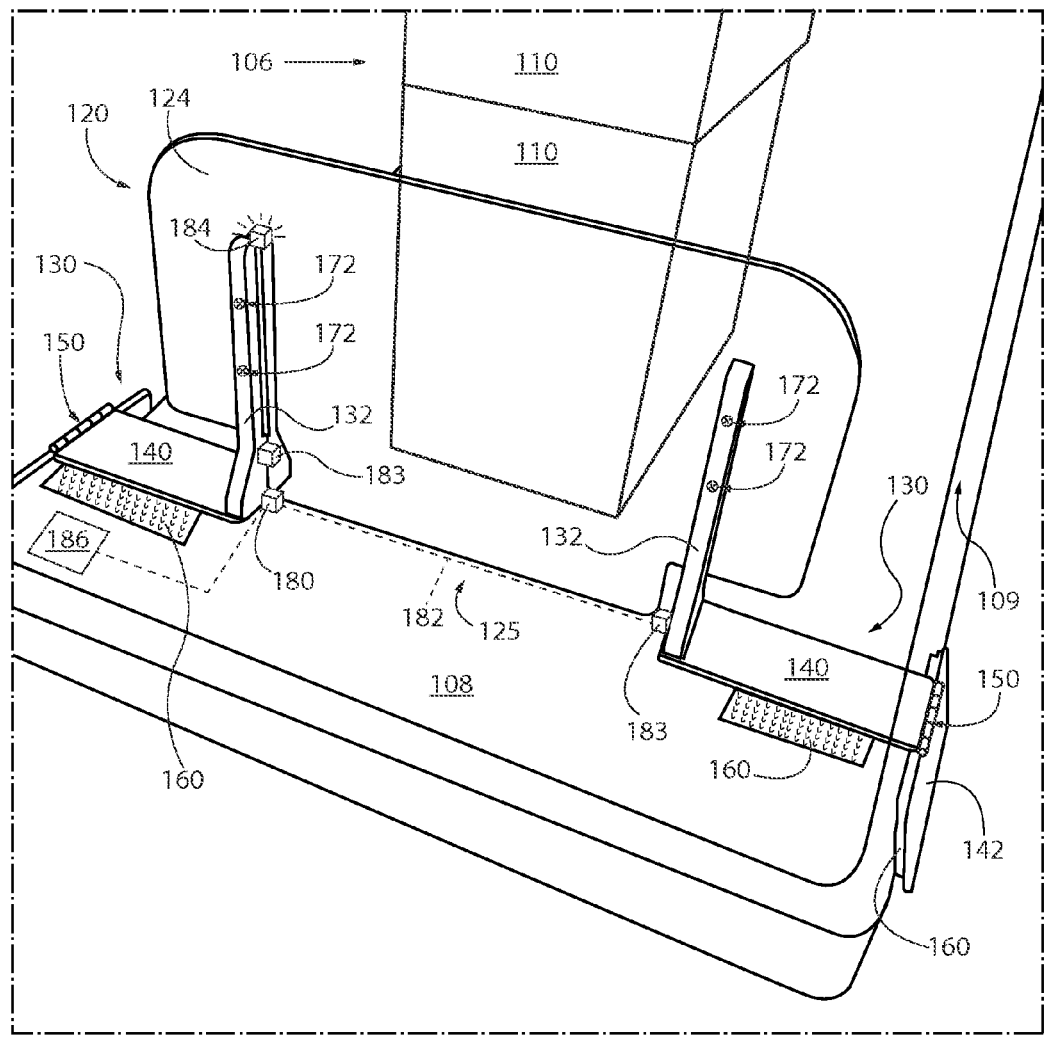
FIG. 4 illustrates a detailed perspective view of another example shroud guard mounted upon another example surgery table.

Each attachment member 130 can be substantially flat, or can include a geometry corresponding to the table base 104, such as an L-shaped geometry (as shown). It can be beneficial to use a L-shaped or other multi-axis geometry to enable the attachment member 130 to attach to the table base 104 at multiple points, such as to either or both of the base surface 108 and side surface 109. If an L-shaped geometry is used, the attachment member 130 can include two members 140, 142 arranged substantially perpendicular to each other, or at other angles. For example, the horizontal member 140 can be substantially co-planar with the base surface 108, while the vertical member 142 can be substantially co-planar with the side surface 109. The two members 140, 142 can be attached to each other variously, such as via screws or other fasteners, adhesives, welding, etc. or even formed together as a monolithic body. In a further example, the L-shaped geometry of the attachment member 130 can be structured so that the two members 140, 142 are pivotally adjustable relative to each other, such as with the two members being secured together by a hinge 150 or the like. The pivotable nature of the two members 140, 142 can be useful to enable the attachment member 130 to be mounted upon different operating room tables that often have different table base geometries. For example, see the different table base geometries of FIGS. 4-5. The table base of FIG. 4 has a substantially perpendicular relationship between the base surface 108 and the side surface 109, whereas the table base of FIG. 5 has a sloped, non-perpendicular relationship (e.g., 120 degrees) between the base surface 108 and the side surface 109. The use of the hinge 150 enables the same attachment member 130 to be used interchangeably with both tables. It is contemplated that the support frame can freely pivot (e.g., between 0°-90°, 0°-135°, 0°-180°, etc.) or can be keyed to pivot to one or more predetermined angles (e.g., 0°, 30°, 45°, 60°, 90°, 135°, 180°, etc.). Preferably, the hinge 150 has an angular range of motion of at least 90 degrees between the two members 140, 142, and more preferably at least 135 degrees. In this manner, the two members 140, 142 can be positioned at most any desired relative angle to accommodate the base surface 108 and side surface 109 of any table base 104 of a particular surgical table 100. This can be beneficial where the outer edges of the table base 104 are rounded or curved, where the base surface 108 is curved, angled, or otherwise not flat, and/or where the transition between the base surface 108 and the side surface 109 is curved, angled, or otherwise not at a 90 degree angle. In another example, instead of a single angle, the L-shaped geometry between the members 140, 142 could further be provided with a modified curved "L" profile to accommodate the various curves, angles, etc. of the table base 104 or base surface 108 or edges thereof. As can be appreciated, the configuration of the attachment member 130 may vary with the associated profile of a surgical table.

Preferably, the attachment member 130 is removably attached to the table base 104 by a fastener 160. The fastener 160 inhibits movement of the attachment member 130, and thereby the entire shroud guard 120, along multiple axes, including a longitudinal axis and transverse axis of the table base 104. In one example, shown in FIG. 1, the fastener can be repositionable, such as a hook-and-loop type fastener or non-permanent adhesive (e.g., double-sided tape or pressure sensitive adhesive) applied to the underside of the attachment member 130 (i.e., to the underside 141 of the horizontal member 140) and to the top of the base surface 108. Where the attachment member 130 has two or more surfaces (such as a L-shaped geometry), the fastener 160 is applied to at least one such surface, and preferably to all such surfaces (i.e., to the underside 141 of the horizontal member 140 for connection to the base surface 108, and to the interior side 143 of the vertical member 142 for connection to the side surface 109). Still, in other examples, it is contemplated that the fasteners 160 may be applied to only the horizontal member 140 and the base surface 108, while the vertical member 142 may instead be provided with a non-abrasive cushion or foam stabilizers. In the case of a repositionable fastener 160, the compatible fastener may extend a substantial distance along the base surface 108 and/or side surface 109 greater than that used by the attachment member 130 to enable the position of the shroud guard 120 to be longitudinally and laterally adjustable to a desired location relatively closer or farther from the telescoping shroud 110 of the surgical table.

These various configurations can enable the attachment member 130 to be secured to the table along a single or multiple axes and surfaces. In other examples, the fastener can include snaps, hooks, clasps, clips, elastic members, tape, other adhesives, etc. or combinations thereof. In still other examples, the attachment member 130 can be secured to the table base 104 by nuts, bolts, screws, etc. In still a further example, the attachment member 130 can be attached to the base surface 108 and/or side surface 109 by the use of magnets. The attachment member 130 can include a magnet for direct magnetic attraction to a compatible metal material of the base surface 108 and/or side surface 109, or indirect magnetic attraction via opposite polarity magnets can be applied to the base surface 108 and/or side surface 109.

Each attachment member 130 further includes a shield support 132 extending upwards and proud therefrom (and relative to the base surface 108) to retain and support the shield 124 in a position to protect the shroud 110. In the shown example, the shield support 132 can be secured to and extend upwards from the horizontal member 140, although it is possible that it could instead be connected to the vertical member 142. The shield 124 can be rigidly secured to the shield support 132 in a removable or non-removable manner. In one example, an upper end 133 of the shield support 132 can include a channel 134 or groove formed therein to at least partially receive the shield 124. The channel 134 or groove is shaped and dimensioned with suitable geometry to be compatible for easy insertion of the shield 124 therein. The channel 134 or groove can be open at the upper end 133, and can extend between two arms 135. In this regards, the channel 134 can have a generally U-shaped geometry. Preferably, the channel is dimensioned to receive the shield 124 between the two arms with a relatively small tolerance, such as less than or equal to about 1 millimeter. In this manner, the shield is not too tightly received, but also has little play within the channel 134 so as to provide an effective barrier to keep foreign objects away from the height adjustment mechanism of the table. The channel 134 can also be closed at a bottom end so that the shield 124 can rest thereupon. The bottom end of the channel 134 can be positioned a predetermined distance above the attachment member 130 to thereby space the bottom edge of the shield a desired distance above the base surface 108 of the table base 104. The channel 134 preferably has a width slightly wider than the thickness of the shield 124 to facilitate sliding therein. In other examples, the channel 134 and shield 124 can each have a mating dovetail geometry that permits relative sliding movement while also providing retention within the channel 134, although various other geometries are contemplated. For example, the dovetail geometry could include a wedge-shaped, "T"-shaped or "I-beam"-shaped geometry with an enlarged head that fits into a recessed channel having a reduced cross-sectional profile that the dovetail to slide therein while resisting or preventing lateral removal of the enlarged head from the channel recess. In another alternative, where no channel is used, a side surface of at least one of the arms 135 may have a recess that extends inwards from one side, and the shield 124 can be located within the recess and secured to at least one arm 135. In still another alternative where no channel is used, the shield 124 could simply be secured to an outer side of at least one arm 135.

The channel 134 can be open at the upper end 133 so that the shield 124 can be slidably received therein. This configuration provides numerous benefits, including height adjustability of the shield 124 relative to the arms 135 of the attachment member 130 (and table base 104), as well as side-to-side adjustability to accommodate various surgical tables having various base configurations and height adjustment mechanisms. The height of the shield 124 can be height adjustable in order to accommodate the patient, accommodate the surgeon or other healthcare workers, and/or to avoid clashing with the patient table surface 102. Additionally, the shield supports 132 are configured to position the shield 124 over table base 104 to be upstanding substantially perpendicular to the base surface 108, although in other examples the shield supports 132 and/or channel 134 can position the shield 124 to extend over the base surface 108 at various other angles.

The shield 124 is removably or non-removably secured to the shield supports 132 by a fastener. In one example, the shield 124 can be coupled to the shield supports 132 via one or more non-permanent fasteners that are received within one or more mounting points or holes. Preferably, the fasteners are operable without the use of tools, such as thumbscrews 170, pins, cam locks, or the like (see FIG. 3). These types of fasteners enable quick and easy assembly/disassembly and maintenance. Alternatively, the shield 124 can be coupled to the shield supports 132 via one or more set screws 172 or the like (see FIG. 4), which may be partially or wholly recessed. These types of fasteners are anti-tamper and inhibit accidental removal of the shield 124. The fasteners can extend through one of the arms 135 of the shield support 132 for direct or indirect contact with the shield 124. Preferably, the fasteners (such as a thumbscrew 170 or set screw 172) apply a compression force against the face of the shield 124 and within the channel 134 to maintain the desired position. The compression force could be direct, where the fastener directly contacts the shield 124, or indirect, where the fastener presses an intermediate body against the shield 124. The use of an indirect body may be beneficial to avoid scratching or otherwise applying a point load to the shield. In another example, the lateral and/or vertical position of the shield 124 can be adjusted to discrete positions (such as 2, 3, 4 or more positions) with regards to the attachment member 130 by selectively positioning the one or more fasteners in different holes on the shield 124, or can even be infinitely adjustable within a range of positions (e.g., where the fasteners are received in a slot of the shield). Optionally, the fastener could include a removable pin that is static or even resiliently biased into locking engagement with at least one of a plurality of holes extending through the shield 124, such as by a spring pin or the like. This provides the removable pin as resiliently biased in the locked position, such that an affirmative action (i.e., pulling on the pin) is used to unlock the shield. The removable pin could extend through the arms 135 of the shield support 132 and through the shield 124, or could alternatively extend only through the arms 135 to close off the upper end 133 of the channel 134 to prevent removal of the shield 124 therefrom. It is further contemplated that other sliding mechanisms can also be used for adjusting the lateral or vertical position of the shield 124, such as linear slides, ball-bearing slides, telescoping slides, geared slides, etc.

Figure 5:
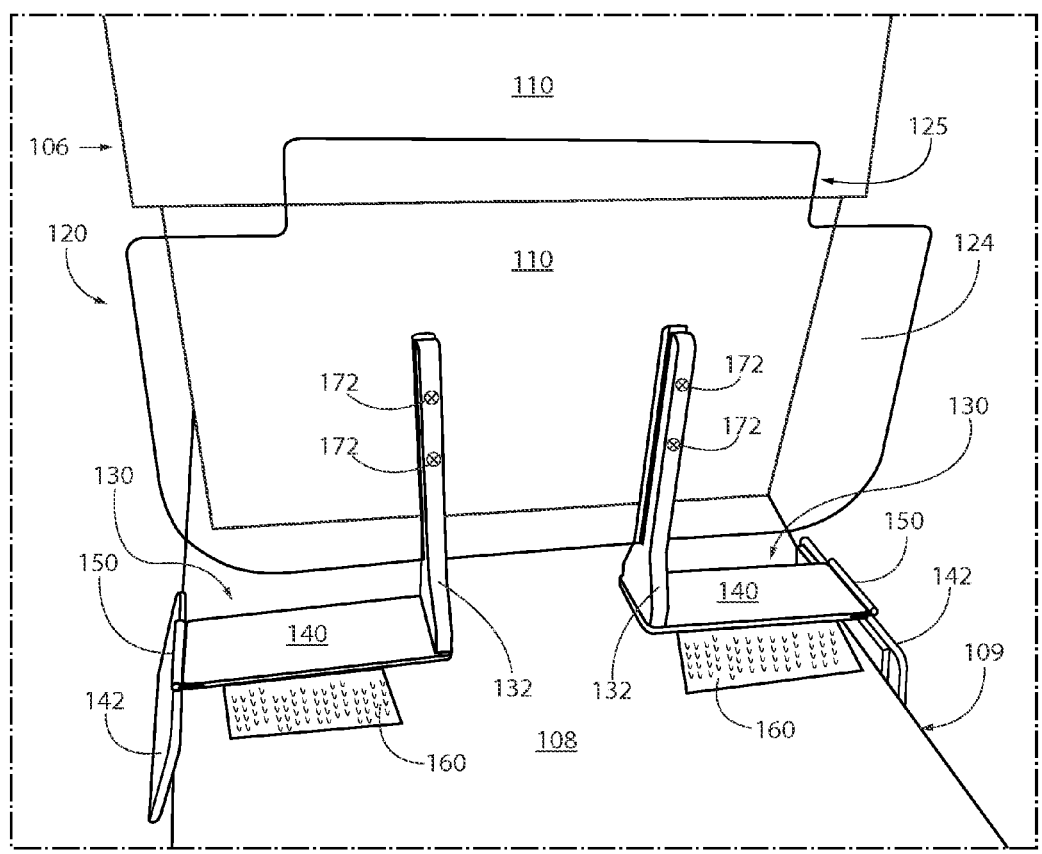
FIG. 5 illustrates a detailed perspective view of the example shroud guard of FIG. 4 mounted upon a relatively narrower surgery table.

In addition to the above, the shield 124 can have various shapes. As shown in FIG. 3, the shield 124 may have a generally rectangular geometry that terminates about the bottom of the channel 134 or groove. Preferably, the corners of the shield 124 are curved to avoid snagging against clothing, surgical drapes, cables, etc. In other examples, shown in FIGS. 4-5, the shield may have a T-shaped geometry with a depending portion 125 that extends further downwards between the attachment members 130 and lower than the channel 134 or groove. In this manner, the depending portion 125 allows the shield 124 to be relatively closer to the base surface 108 to inhibit items 112 from moving underneath the shield 124. Still, it is preferable that the depending portion 125 is spaced a distance from the base surface 108 so that the shroud guard 120 can accommodate multiple surgical tables 100. Additionally, the transition between the main body of the shield 124 and the deepening portion 125 creates a natural shoulder on both sides that can help to align the shield 124 between, or otherwise provide a limit to the lateral adjustability of the shield 124 relative to, the attachment members 130. Additionally, the shield 124 can be flipped upside down in order to accommodate surgical tables with a relatively narrower table base 104. For example, where a surgical table has a relatively narrower table base as shown in FIG. 5, the attachment members 130 are placed relatively more close to each other as compared to the example of FIG. 4. The attachment members 130 are placed closer to each other than the width of the depending portion 125 of the shield 124. Thus, in order to use the same attachment members 130 and shield 124 on the table of FIG. 5, the shield 124 can be removed and rotated 180 degrees upside down so that the top edge of the shield is received within the channels 134 of the shield supports 132. Various other geometries are contemplated.

The shield 124 can include various materials, shapes, etc. Preferably, the shield 124 is a relatively planar configuration to at least partially cover and protect the shroud 110 against contact from foreign items 112 located on the table base 104. The shield 124 may be entirely flat, partially or wholly curved or angled, etc. Various materials can be used for the shield 124, such as various metals (e.g., stainless steel, aluminum, etc.) and plastics, and may or may not be radiolucent. The shield 124 may be opaque, translucent, or transparent. In one example, the shield 124 can be made of ¼ inch to ⅜ inch thick sheet (other thicknesses contemplated) of transparent plastic (such as Plexiglas or the like) so that the shroud 110 (and any indicia thereon) is readily visible through the shield 124. The shield 124 may be colored, and/or may include various indicia thereon (such as instructions, warnings, or the like). Preferably, the shield 124 is of a relatively softer material as compared to the shield supports 132, such as a plastic insert received in a metal channel or an aluminum insert in a steel channel, etc., to facilitate sliding therebetween.

The support frame 122 will work on all surgical tables either at the Head end of table, or Foot end of table, or both at the same time. Moreover, two or more shroud guards can be used on each table, such as on opposed sides of the telescoping shroud to provide protection from multiple sides. Additionally, the shroud guard can be configured to protect some or even the entire perimeter of the height adjustment mechanism by providing a fence that extends around three or even all four sides (or more sides, if desired). For example, the support frame 122 could include additional shield supports that are oriented to position additional shield(s) along the sides of the height adjustment mechanism. In one configuration, two shroud guards 120 could be used on the table base with one at the head end of table and the other at the foot end of table, each including a shield to protect the height adjustment mechanism from those angles. Additionally, each of these shroud guards could further include corresponding side shield supports so that additional side shields can be connected therebetween to protect the lateral sides of the height adjustment mechanism, thereby providing a square or rectangular perimeter guard. In still yet another variation, the shield supports can have a channel 134 with a "X"-shaped geometry (or "+"-shaped) with multiple openings that may be perpendicular or arranged at other angles. In this manner, the X-shaped channel can be more universal to permit a shield to be mounted at various angles, which can be beneficial to use a single part to arrange the shields across different sides of the height adjustment mechanism. It is further contemplated that two or more shields could even be connected to a single channel 134. When assembling the shroud guard 120 upon the table base 104 of the operating room table 100, the various elements can be connected together in different orders. In one example, the complete shroud guard 120 including both the support frame 122 and shield 124 previously assembled can be secured to the table base 104 as one unit. Alternatively, either or both brackets of the support frame 122 can be individually secured to the table base 104, and then the shield 124 can be secured to the brackets. In another alternative, the shield 124 can be secured to one bracket first, and then that bracket can be secured to the table base. Thereafter, the second bracket can be secured to the table base and the other end of the shield. As can be appreciated, the exact order of assembly steps can be various and may depend upon the particular operating room table and use conditions. Although a pair of brackets is shown, it is understood that in an alternative embodiment the support frame 122 can be a single unit that extends transversely over the top surface 108 of the table base 104. For example, the support frame 122 can be a monolithic body that includes both a support fame and shield, such as an L-shape, T-shape, H-shape, C-shape, U-shape, etc.

It is contemplated that the support frame 122 and shield 124 can be height adjustable in order to accommodate the geometry of the surgical table, accommodate the medical personnel, and/or to avoid contact with other medical goods used during a surgical procedure. For example, the support frame 122 and shield 124 can be of a fixed height above the table base 104 that is standardized, and/or that will avoid contact with the patient table surface 102 even when it is lowered to its lowest position.

It is further contemplated that the shroud guard 120 could include an electronic sensor 180, such as an infrared sensor, laser, ultrasonic sensor, light sensor, touch sensor, proximity sensor, tilt sensor, accelerometer, etc. The electronic sensor 180 can determine if foreign objects are in contact with the shroud guard 120 or have passed beyond a predetermined threshold (i.e., beyond the shroud guard and towards the height adjustment mechanism). Such an electronic sensor 180 can be useful to detect foreign objects (or portions thereof) that are leaning upon the shroud guard, and/or might go underneath or around the boundary established by the shroud guard. In one example, the electronic sensor 180 could be an infrared sensor fixed to one of the support frames 122 or shield 124. The infrared sensor could emit a beam of infrared light 182 between the brackets, and can trigger an alarm if an item interferes with the beam. The beam of infrared light could be sensed by a suitable sensing unit 183, which could be located opposite an infrared emitter, or on the same side/at another location through the use of mirror(s), etc. The electronic sensor 180 could trigger various alarms. In one example, the shroud guard 120 could include visual and/or audible alarms. In one example, a light 184 (such as an LED) could be configured to illuminate the shield 124 by emitting light therethrough. The light 184 could illuminate in a particular color, such as red, if a foreign object is detected by the electronic sensor 180 to alert the user. The light could be static, or flashing randomly or in a pattern. The light 184 could also illuminate other colors, such as green if no objects are detected, or yellow if an object is close to the guard, etc. In this regards, multiple electronic sensors could be used to detect object encroachment at multiple locations, or even in a staged approach to detect relatively how close foreign objects are to the shroud guard.

In addition, the electronic sensor 180 could further include an interface 186 with the electronic controls or power system of the operating room table 100 that control the operation of the height adjustment mechanism 106. The electronic sensor 180 could act as a safety switch or interlock that, via the interface 186, selectively permits or disallows operation of the height adjustment mechanism 106 based upon whether a foreign object is detected. In one example, the interface 186 could enable the electronic sensor 180 to be integrated into the on-board electronic controls of the operating room table 100, so that the electronic controls will use the electronic sensor 180 as an input. Based upon this input, the electronic controls will decide whether to operate the height adjustment mechanism. If a foreign object is detected, the on-board electronic controls will disable the height adjustment mechanism from operation until the foreign object is removed, thereby protecting the shroud 110 from damage. If no foreign object is detected, the height adjustment mechanism will be permitted to operate to raise/lower the table. In another embodiment, the interface 186 could be incorporated into a power control module that can selectively enable or disable power supply to at least the height adjustment mechanism, electronic controls thereof, or even to the entire operating room table. For example, the power control module could be an intermediate device located between the main power supply for the table (i.e., AC/DC power line, battery, solar cell, etc.) and the operating room table. If a foreign object is detected by the electronic sensor 180, the power control module could disable power flow to the operating room table, height adjustment mechanism, or electronic controls thereof so that the height adjustment mechanism is incapable of functioning; once the object is removed, power can be restored. Conversely, when no foreign object is detected, power flow is uninterrupted to the operating room table and component parts. In any event, the electronic sensor 180 could include an independent power supply (i.e., a battery, solar cell, etc.) or could obtain power from the operating room table, the interface 186, or from the main power cable or battery of the operating room table itself.

In further addition to the above, a sterile material may cover the any or all of the elements. A removable sterile covering may be used, and the shroud guard 120 can include structure to secure the sterile covering thereto.

The invention can protect the height adjustment mechanism before, during or after any surgical procedure, and is suitable for use with the operating table arranged at various locations, angles, positions, etc. Moreover, the physical profile of the device is not bothersome to medical personnel during surgery. No other design has attempted to solve these issues in this manner. My unique experience, design background, and intimacy in the marketplace are the reason that I am the only person who has created such a device.

The invention has been described with reference to the example embodiments described above. Modifications and alterations will occur to others upon a reading and understanding of this specification. Examples embodiments incorporating one or more aspects of the invention are intended to include all such modifications and alterations insofar as they come within the scope of the appended claims.

What is claimed is:

1. A shroud guard for protecting a height adjustment mechanism used to raise and lower the height of an operating room table, comprising:
   a support frame secured to a table base of said operating room table, the support frame comprising a bracket with an attachment member and an upstanding shield support secured to the attachment member,
   wherein the attachment member is secured to said table base via a fastener to inhibit movement along a longitudinal axis of said table base; and
   a shield removably secured to the upstanding shield support and extending transversely over said table base of said operating room table and across substantially all of said height adjustment mechanism to thereby inhibit foreign objects from contacting said height adjustment mechanism.

2. The shroud guard of claim 1, wherein the attachment member comprises a horizontal member that is co-planar with a base surface of said table base, and a vertical member that is co-planar with a side surface of said table base.

3. The shroud guard of claim 2, wherein the attachment member comprises an L-shaped geometry.

4. The shroud guard of claim 2, wherein the horizontal member and vertical member are rigidly secured together.

5. The shroud guard of claim 2, wherein the horizontal member and vertical member are pivotally connected via a hinge so that an angle therebetween is selectively adjustable.

6. The shroud guard of claim 2, wherein the horizontal member is secured to said base surface by a repositionable fastener.

7. The shroud guard of claim 2, wherein the vertical member is secured to said side surface by a repositionable fastener.

8. The shroud guard of claim 1, wherein the upstanding shield support comprises a channel extending between a pair of arms, and the channel is dimensioned to receive the shield with a tolerance of less than about 1 millimeter.

9. The shroud guard of claim 8, wherein the channel is open at an upper end of the arms for sliding insertion and removal of the shield.

10. The shroud guard of claim 8, wherein the shield is removably secured to at least one of the arms by a fastener.

11. The shroud guard of claim 10, wherein the fastener comprises one of a thumbscrew and a set screw.

12. The shroud guard of claim 1, wherein the fastener is a repositionable fastener that comprises a hook-and-loop type fastener.

13. The shroud guard of claim 12, wherein the repositionable fastener comprises at least two separate fasteners disposed at separate locations upon said table base.

14. The shroud guard of claim 1, wherein the support frame comprises a pair of separate brackets each independently secured to said table base of said operating room table, and the shield is secured to both brackets.

15. The shroud guard of claim 14, wherein the shield is secured to upstanding shield supports of both brackets.

16. The shroud guard of claim 15, wherein the shield comprises a T-shaped geometry with a depending portion that is located between the upstanding shield supports and that has a width narrower than a transverse width between the upstanding shield supports.

17. A shroud guard for protecting a height adjustment mechanism used to raise and lower the height of an operating room table, comprising:

a support frame secured to a table base of said operating room table, the support frame comprising a first bracket with a first attachment member and a first upstanding shield support secured to the first attachment member, and a second bracket with a second attachment member and a second upstanding shield support secured to the second attachment member, wherein each of the first and second attachment members are independently secured to said table base via repositionable fasteners to inhibit movement along a longitudinal axis of said table base, and wherein each of the first and second upstanding shield supports comprise a channel extending between a pair of arms; and a shield removably secured fasteners to both of the first and second upstanding shield supports by being received within the respective channel of each of the first and second upstanding shield supports, so that the shield extends transversely over said table base of said operating room table and across substantially all of said height adjustment mechanism to thereby inhibit foreign objects from contacting said height adjustment mechanism.

18. The shroud guard of claim 17, wherein each of the first and second attachment members comprises a horizontal member that is co-planar with a base surface of said table base, and a vertical member that is co-planar with a side surface of said table base, and wherein the horizontal member and vertical member of each attachment member are pivotally connected via a hinge so that an angle therebetween is selectively adjustable.

19. The shroud guard of claim 17, wherein the repositionable fasteners comprise a hook-and-loop type fastener.

20. The shroud guard of claim 17, wherein the shield comprises a T-shaped geometry with a depending portion that is located between the upstanding shield supports of the first and second attachment members, and wherein the depending portion has a width narrower than a transverse width between the upstanding shield supports.

* * * * *